(12) United States Patent
Babico

(10) Patent No.: US 11,547,848 B2
(45) Date of Patent: Jan. 10, 2023

(54) HIGH-POWER PULSED ELECTROMAGNETIC FIELD APPLICATOR SYSTEMS

(71) Applicant: Regenesis Biomedical, Inc., Scottsdale, AZ (US)

(72) Inventor: John Y. Babico, Scottsdale, AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 596 days.

(21) Appl. No.: 16/449,133

(22) Filed: Jun. 21, 2019

(65) Prior Publication Data

US 2019/0388676 A1 Dec. 26, 2019

Related U.S. Application Data

(60) Provisional application No. 62/688,168, filed on Jun. 21, 2018.

(51) Int. Cl.
| | | |
|---|---|---|
| *A61N 2/02* | (2006.01) | |
| *A61N 1/04* | (2006.01) | |
| *A61N 1/02* | (2006.01) | |
| *A61N 1/40* | (2006.01) | |
| *A61N 2/00* | (2006.01) | |
| *A61N 1/36* | (2006.01) | |

(52) U.S. Cl.
CPC ........... *A61N 1/0456* (2013.01); *A61N 1/025* (2013.01); *A61N 1/0452* (2013.01); *A61N 1/36014* (2013.01); *A61N 1/40* (2013.01); *A61N 2/006* (2013.01); *A61N 2/02* (2013.01)

(58) Field of Classification Search
CPC .... A61N 1/0452; A61N 1/36014; A61N 2/02; A61N 1/025; A61N 1/40; A61N 1/0456; A61N 2/006
See application file for complete search history.

(56) References Cited

U.S. PATENT DOCUMENTS

| | | | |
|---|---|---|---|
| 4,926,881 A | 5/1990 | Ichinomiya et al. | |
| 5,000,178 A | 3/1991 | Griffith | |
| 5,314,401 A | 5/1994 | Tepper | |
| 6,162,166 A | 12/2000 | Neuwirth | |

(Continued)

FOREIGN PATENT DOCUMENTS

| | | |
|---|---|---|
| WO | WO2012/048302 A2 | 4/2012 |
| WO | WO2018/089773 A1 | 5/2018 |

(Continued)

OTHER PUBLICATIONS

Babico; U.S. Appl. No. 17/080,815 entitled Current-based RF driver for pulsed electromagnetic field applicator systems, filed Oct. 26, 2020.

(Continued)

*Primary Examiner* — Christine H Matthews
*Assistant Examiner* — Joshua Daryl D Lannu
(74) *Attorney, Agent, or Firm* — Shay Glenn LLP

(57) ABSTRACT

Described herein are high-power pulsed electromagnetic field (PEMF) applicator apparatuses. These apparatuses are configured to drive multiple applicators to concurrently deliver high-power PEMF signals to tissue. The apparatuses may be further configured to wirelessly communicate with local computing device and a remote server for patient monitoring, prescription and/or device servicing.

15 Claims, 9 Drawing Sheets

(56) References Cited

U.S. PATENT DOCUMENTS

| | | | |
|---|---|---|---|
| 6,174,276 | B1 | 1/2001 | Blackwell |
| 6,261,221 | B1 | 7/2001 | Tepper et al. |
| 6,334,069 | B1 | 12/2001 | George et al. |
| 6,443,883 | B1 | 9/2002 | Ostrow et al. |
| 6,463,336 | B1 | 10/2002 | Mawhinney |
| 6,967,281 | B2 | 11/2005 | George et al. |
| 6,974,961 | B1 | 12/2005 | George et al. |
| 7,907,701 | B2 | 3/2011 | Anderson |
| 8,195,287 | B2 | 6/2012 | Dacey et al. |
| 10,245,439 | B1 | 4/2019 | Schwarz et al. |
| 10,263,466 | B2 | 4/2019 | Boys et al. |
| 10,441,807 | B2 | 10/2019 | Moffett |
| 2004/0176805 | A1 | 9/2004 | Whelan et al. |
| 2004/0210254 | A1 | 10/2004 | Burnett et al. |
| 2005/0010163 | A1 | 1/2005 | Aoki et al. |
| 2005/0059153 | A1 | 3/2005 | George et al. |
| 2007/0060981 | A1 | 3/2007 | Pilla et al. |
| 2008/0004904 | A1* | 1/2008 | Tran ............... A61B 5/6804 705/2 |
| 2008/0249350 | A1 | 10/2008 | Marchitto et al. |
| 2009/0228071 | A1* | 9/2009 | Bourget ............ A61N 1/05 607/60 |
| 2011/0065976 | A1 | 3/2011 | Chornenky et al. |
| 2011/0112352 | A1 | 5/2011 | Pilla et al. |
| 2011/0196365 | A1 | 8/2011 | Kim et al. |
| 2012/0302821 | A1 | 11/2012 | Burnett |
| 2013/0190599 | A1 | 7/2013 | Wyeth et al. |
| 2013/0245486 | A1* | 9/2013 | Simon ............. A61B 5/4041 600/546 |
| 2014/0012108 | A1 | 1/2014 | McPeak |
| 2014/0148870 | A1 | 5/2014 | Burnett |
| 2014/0213844 | A1* | 7/2014 | Pilla ............... A61N 2/008 600/14 |
| 2014/0249355 | A1 | 9/2014 | Martinez |
| 2014/0265611 | A1* | 9/2014 | Fern .............. H02J 7/00034 307/104 |
| 2014/0336443 | A1* | 11/2014 | Maharaj ........... A61P 43/00 600/13 |
| 2015/0297910 | A1* | 10/2015 | Dimino ........... A41D 13/1245 600/14 |
| 2016/0015995 | A1* | 1/2016 | Leung ............. A61N 2/02 600/14 |
| 2016/0346561 | A1 | 12/2016 | Ron Edoute et al. |
| 2018/0001102 | A1 | 1/2018 | Henry et al. |
| 2018/0043174 | A1 | 2/2018 | Gurfein |
| 2018/0071545 | A1 | 3/2018 | Saitoh et al. |
| 2018/0126185 | A1 | 5/2018 | Hochstenbach |
| 2018/0318598 | A1 | 11/2018 | Russo et al. |
| 2019/0290925 | A1 | 9/2019 | Gellman et al. |
| 2020/0001101 | A1 | 1/2020 | Moffett |
| 2020/0139120 | A1 | 5/2020 | Rajguru et al. |
| 2020/0206523 | A1 | 7/2020 | Kirk et al. |
| 2020/0360710 | A1 | 11/2020 | Anderson et al. |
| 2021/0023382 | A1 | 1/2021 | Kirk et al. |
| 2021/0085180 | A1 | 3/2021 | Jung et al. |
| 2022/0118268 | A1 | 4/2022 | Kirk et al. |

FOREIGN PATENT DOCUMENTS

| | | |
|---|---|---|
| WO | WO2019/023265 A1 | 1/2019 |
| WO | WO2019/183622 A1 | 9/2019 |

OTHER PUBLICATIONS

Akan et al.; Extremely low-frequency electromagnetic fields affect the immune response of monocyte-derived macrophages to pathogens; Bioelectromagnetics; 31(8); pp. 603-612; Dec. 2010.

Apfelbaum et al.; Postoperative pain experience: results from a national survey suggest postoperative pain continues to be undermanaged; Anesthesia and Analgesia; 97(2); pp. 534-540; Aug. 2003.

Baranano et al.; Biliverdin reductase: a major physiologic cytoprotectant; Proceedings of the National Academy of Sciences; 99(25); pp. 16093-16098; Dec. 10, 2002.

Basbaum et al.; Cellular and molecular mechanisms of pain; Cell; 139(2); pp. 267-284; Oct. 16, 2009.

Brennan et al.; Cytokine expression in chronic inflammatory disease; British Medical Bulletin; 51(2); pp. 368-384; Apr. 1995.

Buckley et al.; The resolution of inflammation; Nature Reviews Immunology; 13(1); pp. 59-66; Jan. 2013.

Catala; Five decades with polyunsaturated Fatty acids: chemical synthesis, enzymatic formation, lipid peroxidation and its biological effects; Journal of Lipids; http://dx.doi.org/10.1155/2013/710290; 20 pages; (year of pub. sufficiently earlier than effective US filing date and any foreign priority date) 2013.

Clark et al.; Neuropathic pain and cytokines: current perspectives; Journal of Pain Research; 6; pp. 803-814; doi: 10.2147/JPR. S53660; 12 pages; Nov. 21, 2013.

Commins et al.; The extended IL-10 superfamily: IL-10, IL-19, IL-20, IL-22, IL-24, IL-26, IL-28, and IL-29; Journal of Allergy and Clinical Immunology; 121(5); pp. 1108-1111; May 2008.

Dutra et al.; Heme on innate immunity and inflammation; Frontiers in Pharmacology; 5; Article 115; doi: 10.3389/fphar.2014.00115; 20 pages; May 2014.

Gou et al.; Meta-analysis of clinical efficacy of pulsed radio frequency energy treatment; Annals of Surgery; 255(3); pp. 457-467; Mar. 2012.

Greene et al.; Regulation of inflammation in cancer by eicosanoids; Prostaglandins and Other Lipid Mediators; 96(1-4); pp. 27-36; 26 pages; (Author Manuscript); Nov. 2011.

Guo et al.; Pulsed radio frequency energy (PRFE) use in human medical applications; Electromagnetic Biology and Medicine; 30(1); pp. 21-45; Mar. 2011.

Hasegawa et al.; Modifying TNF alpha for therapeutic use: a perpective on the TNF receptor system; Mini Reviews in Medicinal Chemistry; 1(1); pp. 5-16; May 2001.

Haworth et al.; Resolving the problem of persistence in the switch from acute to chronic inflammation; Proceedings of the National Academy of Sciences; 104(52); pp. 20647-20648; Dec. 26, 2007.

He et al.; Exposure to extremely low-frequency electromagnetic fields modulates Na+ currents in rat cerebellar granule cells through increase of AA/PGE2 and EP receptor-mediated cAMP/PKA pathway; Plos One; 8(1); pp. e54376; 13 pages; Jan. 22, 2013.

Heden et al.; Effects of pulsed electromagnetic fields on postoperative pain: a double-blind randomized pilot study in breast augmentation patients; Aesthetic Plastic Surgery; 32(4); pp. 660-666; Jul. 2008.

Ji et al; Emerging roles of resolvins in the resolution of inflammation and pain; Trenads in Neurosciences; 34(11); pp. 599-609; 20 pages; (Author Manuscript); Nov. 2011.

Kunkel et al.; Suppression of acute and chronic inflammation by orally administered prostaglandins; Arthritis and Rheumatism: Official Journal of the American College of Eheumatology; 24(9); pp. 1151-1158; Sep. 1981.

Livak et al.; Analysis of relative gene expression data using real-time quantitative PCR and the 2-??CT method; Methods; 25(4); pp. 402-408; Dec. 2001.

Markov et al.; Interaction between electromagnetic fields and the immune system: possible mechanisms for pain control; Ayrapetyan SNM, M.S., ed.; Bioelectromagnetics Current Concepts; Dordrecht: Springer; pp. 213-225; (year of pub. sufficiently earlier than effective US filing date and any foreign priority date) 2006.

McIntyre et al.; Molecular mechanisms of early inflammation; Thromb Haemost; 78(I):302-305; Jul. 1997.

Medzhitov et al.; Transcriptional control of the inflammatory response; Nature Reviews Immunology; 9(10); pp. 692-703; Oct. 2009.

Medzhitov: Origin and physiological roles of inflammation; Nature; 454(7203); pp. 428-435; Jul. 23, 2008.

Medzhitov; Inflammation 2010: new adventures of an old flame; Cell; 140(6); pp. 771-776; Mar. 19, 2010.

Moffett et al.; Activation of endogenous opioid gene expression in human keratinocytes and fibroblasts by pulsed radiofrequency energy fields; Journal of Pain Research; 5; pp. 347-357; Sep. 19, 2012.

Moffett et al.; Pulsed radio frequency energy field treatment of cells in culture results in increased expression of genes involved in angiogenesis and tissue remodeling during wound healing; The

(56) References Cited

OTHER PUBLICATIONS

Journal of Diabetic Foot Complications; 3(2); pp. 30-39; (year of pub. sufficiently earlier than effective US filing date and any foreign priority date) 2011.
Moffett et al.; Pulsed radio frequency energy field treatment of cells in culture results in increased expression of genes involved in inflammation phase of lower extremity diabetic wound healing; The Journal of Diabetic Foot Complications; 2(3); pp. 57-64; (year of pub. sufficiently earlier than effective US filing date and any foreign priority date) 2010.
Moreland; Inhibitors of tumor necrosis factor for rheumatoid arthritis; 66(6); pp. 367-374; Jun. 1999.
Moreland; Inhibitors of tumor necrosis factor for rheumatoid arthritis; The Journal of Rheumatology; 57; pp. 7-15; May 1, 1999.
Mosser et al.; Interleukin-10: new perspectives on an old cytokine; Immunological Reviews; 226(1); pp. 205-218; 22 pages; (Author Manuscript); Dec. 2008.
Nathan; Nonresolving inflammation; Cell; 140(6); pp. 871-882; Mar. 19, 2010.
Neher et al.; Molecular mechanisms of inflammation and tissue injury after major traumais complement the "bad guy"?; Journal of Biomedical Sciences; 18(1); pp. 90; doi: 10.1186/1423/1423-0127-18-90; Dec. 2011.
Novo et al.; Redox mechanisms in hepatic chronic wound healing and fibrogenesis; Fibrogenesis and tissue repair; 1(1); doi:10.1186/1755-1536-1-5; 58 pages; Dec. 2008.
Pelletier et al.; New tricks from an old dog: mitochondria) redox signaling in cellular inflammation; InSeminars in Immunology; 24(6); pp. 384-392; 21 pages; (Author Manuscript); Dec. 2012.
Pilla et al.; EMF signals and ion/ligand binding kinetics: prediction of bioeffective waveform parameters; Bioelectrochemisrty and Bioenergetics; 48(1); pp. 27-34; Feb. 1999.
Pilla et al.; Nonthermal electromagnetic fields: from first messenger to therapeutic applications; Electromagnetic Biology and Medicine; 32(2); pp. 123-136; Jun. 2013.
Pons et al.; Pro-inflammatory and anti-inflammatory effects of the stable prostaglandin D2 analogue; European Journal of Pharmacology; 261(3); pp. 237-247; Aug. 22, 1994.
Rohde et al.; Effects of pulsed electromagnetic fileds on interleukin-1 beta and postoperative pain: a double-blind, placebo-controlled, pilot study in breast reduction patients; Plastic and Reconstructive Surgery; 125(6); pp. 1620-1629; Jun. 2010.
Ross et al.; Effect of time-varied magnetic field on inflammatory response in macrophage cell line RAW 264.7; Electromagnetic Biology and Medicine; 32(1); pp. 59-69; Mar. 2013.
Ross et al.; Effect of pulsed electromagnetic field on inflammatory pathway markers in RAW 264.7 murine macrophages; Journal of Inflammation Research; 6; pp. 45-51; (year of pub. sufficiently earlier than effective US filing date and any foreign priority date) 2013.
Selvam et al.; Low frequency and low intensity pulsed electromagnetic field exerts its antinflammatory effect through restoration of plasma membrane calcium; Life Sciences; 80(26); pp. 2403-2410; Jun. 6, 2007.
Serhan et al.; Anti-inflammatory and proresolving lipid mediators; Annu. Rev. Pathmechdis. Mech. Dis.; 3; pp. 279-312; 43 pages; (Author Manuscript); Feb. 28, 2008.
Serhan et al.; Maresins: novel macrophage mediators with potent anti-inflammatory and proresolving actions; Journal of Experimental Medicine; 206(1); pp. 15-23; Jan. 16, 2009.
Serhan et al.; Protectins and maresins: New pro-resolving families of mediators in acute inflammation and resolution bioactive metabolome; Biochimica et Bipphysics Acta (BBA)—Molecular and Cell Biology of Lipid; 1851(4); pp. 397-413; 40 pages; (Author Manuscript); Apr. 30, 2015.
Serhan; Novel lipid mediators and resolution mechanisms in acute inflammation: to resolve or not?; The American Journal of Pathology; 177(4); pp. 1576-1591; Oct. 2010.
Serhan; Novel pro-resolving lipid mediators are leads for resolution physiology; Nature; 510(7503); pp. 92-101; 24 pages; (Author Manuscript); Jun. 2014.
Cho et al.; Discovery of (2-fluoro-benzyl)-(2-methyl-2 phenethyl-2H-chromen-6-yl)-amine (KRH-102140) as an orally active 5-lipoxygenase inhibitor with activity in murine inflammation models; Pharmacology; 87(1-2); pp. 49-55; Feb. 2011.
Spite et al.; Resovins, specialized proresolving lipid mediators, and their potential roles in metabolic diseases; Cell Metabolism; 19(1); pp. 21-36; Jan. 7, 2014.
Srhan et al.; Resolving inflammation: dual anti-inflammatory and pro resolution lipid mediators; Nature Reviews Immunology; 8(5); pp. 349-361; 31 pages; (Author Manuscript); May 2008.
Stein et al.; Peripheral mechanisms of pain and analgesia; Brain Research Reviews; 60(1); pp. 90-113; 38 pages; (Author Manuscript); Apr. 2009.
Suleyman et al.; Anti-inflammatory and side effects of cyclooxygenase inhibitors; Pharmacological Reports; 59(3); pp. 247-258; May 2007.
Uddin et al.; Resolvins: natural agonists for resolution of pulmonary inflammation; Progress in Lipid Research; 50(1); pp. 75-88; 30 pages; (Author Manuscript); Jan. 31, 2011.
Vilcek; The cytokines: an overview; In: Thomson WAaMTL, ed.; The Cytokine Handbook. 4 ed. San Diego: Academic Press, Calif, USA; pp. 1-18; (year of pub. sufficiently earlier than effective US filing date and any foreign priority date) 2012.
Wagener et al.; Different faces of the heme-heme oxygenase system in inflammation; Pharmacological Reviews; 55(3); pp. 551-571; Sep. 2003.
Wagener et al.; The heme-heme oxygenase system: a molecular switch in wound healing; Blood; 102(2); pp. 521-528; Jul. 15, 2003.
Wegiel et al.; Go green: the anti-inflammatory effects of biliverdin reductase; Frontiers in Pharmacology; 3; Article 47; doi: 10.3389/fphar.2012.00047; 8 pages; Mar. 16, 2012.
Xu et al.; Resolvins RvE1 and RvD1 attenuate inflammatory pain via central and peripheral actions; Nature Medicine; 16(5); pp. 591-597; 10 pages; (Author Manuscript); May 2010.
Yang et al.; Metabolomics-lipidomics of eicosanoids and docosanoids generated by phagocytes; Current Protocols in Immunology; 95(1); pp. 14-26; 36 pages; (Author Manuscript); Nov. 2011.
Yang et al.; Reactive oxygen species in the immune system; International Reviews of Immunology; 32(3); pp. 249-270; Jun. 2013.
Yeretssian et al; Molecular regulation of inflammation and cell death; Cytokine; 43(3); pp. 380-390; Sep. 2008.

\* cited by examiner

HIGH-POWER PULSED ELECTROMAGNETIC FIELD APPLICATOR SYSTEMS

CROSS REFERENCE TO RELATED APPLICATIONS

This patent application claims priority to U.S. Provisional Patent Application No. 62/688,168, filed on Jun. 21, 2018, and titled "HIGH-POWER PULSED ELECTROMAGNETIC FIELD APPLICATOR SYSTEMS," which is herein incorporated by reference in its entirety.

The following U.S. patent applications are also herein incorporated by reference in their entirety to the same extent as if each individual publication or patent application was specifically and individually indicated to be incorporated by reference: U.S. Pat. No. 6,334,069, titled "PULSED ELECTROMAGNETIC ENERGY TREATMENT APPARATUS AND METHOD," filed on Jan. 15, 1999, U.S. Pat. No. 6,353,763, titled "PULSED ELECTROMAGNETIC ENERGY TREATMENT APPARATUS AND METHOD," filed on Jun. 27, 2000, U.S. Pat. No. 6,967,281, titled "COVER FOR ELECTROMAGNETIC TREATMENT APPLICATOR," filed on Oct. 22, 2003, U.S. Pat. No. 6,974,961, titled "COVER FOR ELECTROMAGNETIC TREATMENT APPLICATOR," filed on Sep. 14, 2000, U.S. Pat. No. 7,024,239, titled "PULSED ELECTROMAGNETIC ENERGY TREATMENT APPARATUS AND METHOD," filed on Nov. 20, 2001, and PCT Patent Application No. PCT/US2015/062232, titled "TREATMENT OF CONDITIONS SUSCEPTIBLE TO PULSED ELECTROMAGNETIC FIELD THERAPY," filed on Nov. 23, 2015.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to pulsed electromagnetic field (PEMF) systems, apparatuses and methods. In particular, the disclosure relates to high-power pulsed electromagnetic field (PEMF) applicator systems.

BACKGROUND

Pulsed electromagnetic fields (PEMF) have been described for treating therapeutically resistant problems of both the musculoskeletal system as well as soft tissues. PEMF typically includes the use of low-energy, time-varying magnetic fields. For example, PEMF therapy has been used to treat non-union bone fractures and delayed union bone fractures. PEMF therapy has also been used for treatment of corresponding types of body soft tissue injuries including chronic refractory tendinitis, decubitus ulcers and ligament, tendon injuries, osteoporosis, and Charcot foot. During PEMF therapy, an electromagnetic transducer coil is generally placed in the vicinity of the injury (sometimes referred to as the "target area") such that pulsing the transducer coil will produce an applied or driving field that penetrates to the underlying tissue.

Treatment devices emitting magnetic and/or electromagnetic energy offer significant advantages over other types of electrical stimulators because magnetic and electromagnetic energy can be applied externally through clothing and wound dressings, thereby rendering such treatments completely non-invasive. Moreover, published reports of double blind placebo-controlled clinical trials utilizing a RF transmission device (Diapulse) suggest that this ancillary treatment device significantly reduces wound healing time for chronic pressure ulcers as well as for surgical wounds. Studies using Dermagen, a magnetic device manufactured in Europe which produces a low frequency magnetic field, have demonstrated significant augmentation of healing of venous stasis ulcers. Additionally, it has been shown that 50% fewer patients treated with electromagnetic energy develop reoccurring pressure ulcers, compared to control patients, suggesting that electromagnetic energy treatments impart some resistance to the reoccurrence of chronic wounds, such as pressure ulcers. Electromagnetic energy may also be useful as a preventative strategy. Analysis of the effects of electromagnetic energy on the treatment of pressure ulcers show that this treatment, by reducing healing time by an average of 50%, results in significant reductions in the costs associated with wound management.

Traditional PEMF devices are typically stand-alone units that have limited, if any, communications ability. Described herein are PEMF systems with wireless communications capabilities that allow the PEMF systems to wirelessly communicate with an external computing device, such as a smartphone.

SUMMARY OF THE DISCLOSURE

In general, described herein are high-power pulsed electromagnetic field (PEMF) applicator apparatuses (e.g., devices and systems, including applicators and base units with or without applicators). These apparatuses may include a base unit that includes controller that may couple to one or more applicators. In particular, described herein are apparatuses that are configured to operate a plurality of different applicators from a single base unit by efficiently multiplexing the signal, controlling (including in some variations, with feedback control) and applying high-voltage PEMF from multiple applicators without interfering with the PEMF applied by different applicators.

For example, described herein are high-power pulsed electromagnetic field (PEMF) applicator systems that may include: a base housing comprising a controller configured to generate and multiplex a high-power pulsed signal; and two or more applicators coupled to the base, each applicator comprising: a coil circuit configured to emit the high-power pulsed electromagnetic field signal wherein the high-power pulsed electromagnetic field signal has a power of greater than 40 W; and an electromagnetic energy shield disposed between the drive circuitry and the coil circuit; wherein the two or more controller is configured to apply the multiplexed signal to the two or more applicators so that each applicator emits a PEMF signal without interference.

The two or more applicators are configured to be handheld. As will be described in greater detail below, the two or more applicators may include a feedback circuit positioned behind the coil circuit and configured to detect the field strength of the high-power pulsed electromagnetic field signal emitted by the coil circuit. The controller may be configured to adjust an amplitude of the high-power pulsed electromagnetic field in response to the detected filed strength (e.g., one or more of electric field, magnetic field, or both) by adjusting a control signal (e.g., a low-power control signal), to adjust an RF amplification stage that is connected to, or part of, the controller.

The feedback circuit may be printed on a first side of a printed circuit board and the coil circuit may be printed on an opposite side of the printed circuit board.

In general, each applicator of the one or more applicators may include a tuning/matching circuit. The applicator may be tuned to a specific body part (e.g., head, foot, arm, hand, torso, upper chest, belly, back, leg, ankle, wrist, etc.).

Any appropriate PEMF signal may be applied. For example, the high-power pulsed electromagnetic field signal may have a carrier frequency in the MHz range. For example, the carrier frequency may be between about 6 MHz and 100 MHz (e.g., about 27 MHz, about 10 MHz, between about 10 MHz and 60 MHz, etc.).

Any of the controllers may include a diagnostic unit configured to run diagnosis and generate an error code. Any of the apparatuses, and including any of the controllers of the apparatus, may include a wireless circuitry (e.g., a cellular circuitry or module, Wi-Fi, ZigBee, Bluetooth, etc.), configured to wirelessly communicate with a remote server, either directly or indirectly through an intermediary computing device, such as a smartphone, smartwatch, a tablet computer, a desktop computer, or a laptop computer. In some variations the controller further comprises a radio frequency identification (RFID) reader. The one or more applicators may be identified by an RFID code that may be read by the reader.

In general, the applicators may include a shield board configured to shield one side of the coil circuit. The applicator and/or base may be arranged so that the high-voltage RF energy associated with the RF amplification stages (in the base) and applicators do not interfere (inductively, capacitively, or otherwise) with the operation of the electronics in the device.

As mentioned, any of the apparatuses described herein may be configured to drive one or more applicators that are load-specific. In general, the apparatuses described herein include a tuned switching power amplifier comprising a single-pole switching element that is capable of very efficient operation. For example, described herein are applicators configured to be operated with different body treatment areas; e.g., the load profile of these different applicators may be configured to have different loads, permitting them to be impedance matched to get efficient energy transfer.

One or more loop antennas may be used on the applicator board for inductive coupling to the H-field. This may allow us to specifically control H-field rather than simply the E-field. This approach may also give a more accurate measurement of the field strength produced because H-field is not generally influenced (reflected or absorbed) by the user.

Any of these sensing methods may combine both inductive and capacitive sensing. This may allow control of E- and H-fields independently from each other.

Alternatively or additionally, any of these methods and apparatuses may include optical feedback. For example, and optical emitter and receiver (e.g., an IR emitter and receiver) may be used to detect contact and/or proximity of the applicator to the users skin. This may allow the apparatus to only activate the field when the applicator is in a treatment position.

Any of the apparatuses described herein may include shielding that is textured or patterned, which may increase its effectiveness. For example, any of the PCB shielding described herein may include a cross-hatched PCB (25% coverage in a cross-hatched pattern). Surprisingly, the inventors have found that a PCB with a grounded, cross-hatched copper pattern provided excellent shielding for the radiated E-field and also provided lower EMI/EMC emissions than either a copper solid plane PCB or the aluminum shield often used in many other PEMF products.

As mentioned, any of the apparatuses described herein may include wireless communication capability. For example, any of these apparatuses may include a wireless circuit or circuitry (which may be part of or controlled by the controller) and may be used to provide connectivity to a remote server, and/or for communicating with the user (including sending alerts, data, etc.) and/or for monitoring, operating and updating the system. In some variations the apparatus (e.g., system) may be configured so that patient prescriptions are provided to the device from a physician via communications (e.g. wireless, such as cellular) circuitry on the apparatus.

In some variations, the wireless circuitry may be used to upload therapy field feedback that may indicate operation of the apparatus. This operation may indicate that the apparatus is being used properly (e.g., monitoring compliance) and/or that the apparatus is in working order (e.g., monitoring to prevent miss-operation and/or problems with the system (in the software, firmware, hardware, applicator, base, etc.).

For example, any of these apparatuses may be configured to provide real-time or near real-time monitoring and feedback to users to ensure product effectiveness. The apparatus may also be configured to provide usage validation (e.g., detecting, recording and/or transmitting) when a user is operating the device as prescribed, which may be used for compliance monitoring.

The apparatuses described herein may also be configured to uploaded diagnostics that may allow remote troubleshooting of devices in the field. For example, the apparatus may be configured to download, via the wireless circuitry, one or more software updates in the field, and/or my deliver messages, including alerts, to the user, and/or may be used to deliver a digital prescription for the operation of the apparatus.

For example, also described herein are methods of controlling operation of high-power pulsed electromagnetic field (PEMF) applicator system, the method comprising: emitting a high-power PEMF signal having a power of greater than 40 W from an applicator of the high-power PEMF applicator system, wherein the high-power PEMF applicator system includes: a controller configured to generate a high-power pulsed signal, a power amplifier configured to generate a pulsed drive signal, a wireless communication circuit, and an RF amplification stage configured to couple to the applicator, wherein the applicator includes a coil circuit configured to emit the high-power pulsed electromagnetic field signal and a feedback sensor; receiving a feedback signal in the feedback sensor from the high-power PEMF signal emitted by the applicator; transmitting a therapy field feedback signal derived from or including the feedback signal to a remote server; and transmitting, from the remote server, an alert to a user operating the high-power PEMF applicator system when the therapy field feedback signal exceeds a predetermined set of performance parameters.

Any of these methods may include transmitting, from the remote server, a prescription for additional high-power PEMF signal. For example, the methods may include receiving one or more of: a capacitance signal and an inductance signal. Receiving the feedback signal may comprises receiving a field strength signal indicating the strength of one or more of an applied electrical field or magnetic field. Receiving the feedback signal may comprise receiving a signal indicating contact with a body part.

Transmitting may comprise transmitting via a wireless (e.g., cellular) transmission from the high-power PEMF applicator system. In any of these apparatuses, transmitting the therapy field feedback signal may comprise transmitting to a user wireless communications device and transmitting form the user wireless communications device to the remote server. Transmitting the therapy field feedback signal may comprise transmitting compliance data based on the feedback signal. Transmitting the therapy field feedback signal may comprise transmitting in real time or near real-time (e.g., with less than a 1 minute latency, less than a 30 second latency, less than a 15 second latency, less than a 10 second latency, etc.). Alternatively or additionally, transmitting the therapy field feedback signal may comprises transmitting at the start of a next session of the high-power PEMF applicator system. Any of these methods may include confirming a transmission path before transmitting the therapy field feedback signal (e.g., attempting to transmit one or more times, e.g., 2 times, 3 times, 4 times, etc.).

In general, any of the methods described herein may include metering or controlling the delivery based on a prescription or metering device. For example, the methods described herein can include the step of transmitting a radio frequency identification (RFID) address between the handheld applicator and the base housing. The hand-held applicator may generate the high-power, pulsed electromagnetic field only after the base housing verifies the RFID address.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 8C the antenna coil is a spiral. In FIG. 8D the antenna coil is a spiral having a thickness that varies as the trace helically coils around itself. In this example, the central region is thinner and the trace gets thicker as it spirals outward. The thickness may increase continuously (e.g., from one end of the trace to the other end of the trace). The variation shown in FIG. 8D may be less sensitive to load, and may allow the apparatus to be less sensitive to load variations.

DETAILED DESCRIPTION

Figure 1:
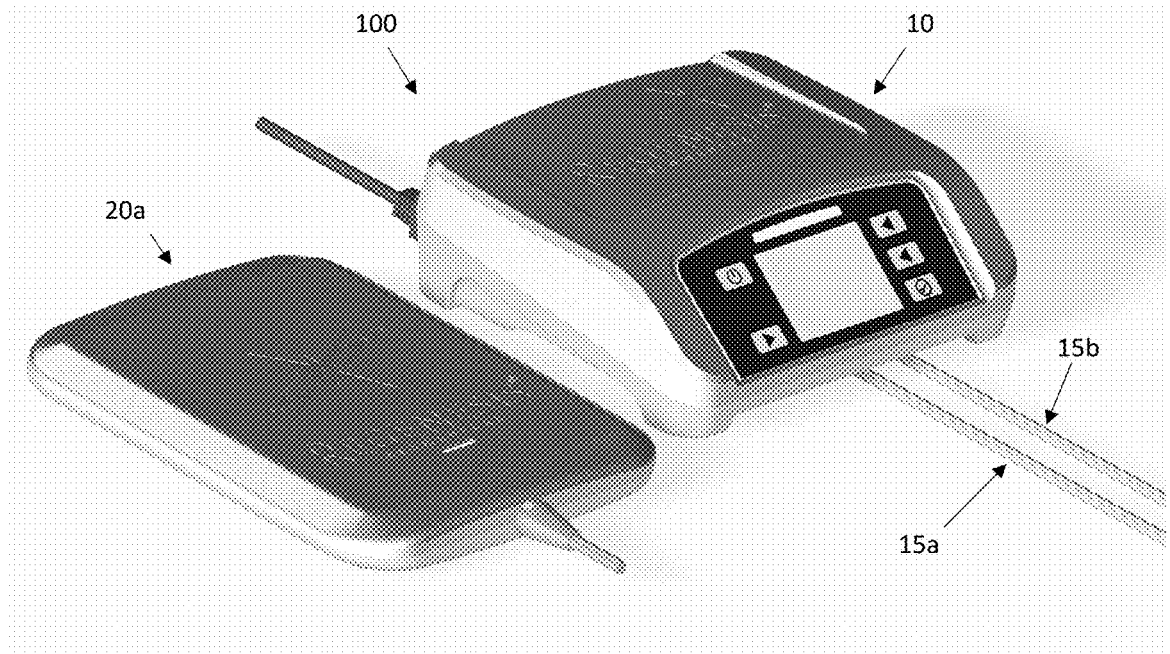
FIG. 1 illustrates one example of a high-power pulsed electromagnetic field (PEMF) applicator system including one applicator.

The present disclosure now will be described in detail with reference to the accompanying figures. This disclosure may be embodied in many different forms and should not be construed as limited to the example embodiments discussed herein.

Described herein are high-power pulsed electromagnetic field (PEMF) applicator apparatuses. In general, the apparatuses described herein are configured to as high-power pulsed electromagnetic field (PEMF) applicator apparatuses. As used herein, an apparatus may include a system and/or a method. These apparatuses may be configured as compact and lightweight apparatuses. The high-power pulsed electromagnetic field (PEMF) applicator apparatuses described herein may be further configured to have multiple applicators for simultaneously treating using the multiple applicators (e.g., dual applicators, three applicators, four applicators, five applicators, six applicators, seven applicators, eight applicators, etc.). These applicators may be configured to asynchronously fire to avoid or eliminate interference between the applicators. For example, the stimulation between different applicators may be multiplexed.

Any of the high-power pulsed electromagnetic field (PEMF) applicator apparatuses described herein may be configured to provide wireless communication (via a cellular or other communications circuitry) to a remote processor and/or a telephonic or computer network. The wireless communication circuitry may permit compliance monitoring, software updates, and client messaging.

The apparatuses described herein are also configured to provide highly efficient amplification of power. These apparatuses may also be configured to prevent thermal build-up in the base unit and/or applicators. Any of the apparatuses described herein may also include a user interface (e.g., user inputs, display, etc.) that is intuitive and configured for robust operation. The user interface may also provide visual indicators of treatment and display of error conditions.

The systems can comprise a base housing including a controller configured to generate a low-power control signal and one or more applicators coupled to the base. Each applicator can include a drive circuitry comprising a generator to produce a high-power, pulsed electromagnetic field signal that is transmitted to an applicator. The high-power pulsed electromagnetic field signal can have a power of greater than 40 W.

Each applicator can further include a coil circuit configured to emit or apply the high-power pulsed electromagnetic field signal.

In general, the apparatuses described herein are configured for concurrent application of two (or more) applied high-power PEMF signals to a patient from two or more applicators. Thus, the base unit may multiplex the applied signals in a manner that prevents cross-interference between applicator fields. Typically, multiplexing may include driving multiple applicators so that applicators may each deliver non-overlapping signals. In some variations, the controller in the base unit may increase the pulsing rate by a multiple of the rate used for delivering a single applicator (e.g., if two applicators are used, the base unit may dynamically double the pulse rate, e.g., from 1000 Hz to 2000 Hz). Each RF amplification stage may receive the same pulsing signals yet be enabled independently and separately from other stages. Each applicator may then pulse at the standard rate (e.g., 1000 Hz) while alternating the application of high-power PEMF between the multiple applicators. Cross interference may be reduced or prevented by having only one applicator active at any time. The RF amplifier stages may be positioned on an RF board within the base unit, so that they may receive control signals and provide the RF pulsed output signals to the applicators. The RF amplifier stages may be controlled by one or more control signs (e.g., from the controller) that may be used to enable one stage (and therefore one amplifier) at a time. The RF amplification stages (e.g., stages 1-8 in some variations) may be addressed individually by the controller to be active, so that only one RF amplification stage having the proper address acts on it. In some variations this may be achieved by providing an enabling signal that enables individual RF amplification stages at a time. Thus, only one amplifier may be active at a time. The activation signals may be separated in time (e.g., only 42 microseconds out of 1000 microseconds). Thus, every amplification stage may receive the same signal from the controller (e.g., a signal generator portion of the controller) and this signal may be transmitted by one of the applicators only when the control signal is 'on' for that applicator, by activating the RF amplification stage in the base unit. By enabling (e.g., using enabling lines) that apparatus may not need to change anything but the rate of the signal, enabling multiplexing of the signal between different applicators.

In some variations, the apparatus may sense that one or more of the applicators is not in appropriate contact or proximity with the patient (e.g., user) and may dynamically adjust the applied signal(s).

In general, each applicator has its own feedback sensor. Thus, each applicator may be individually controlled by a feedback control loop. The feedback may sense the applied field and may be used by the RF amplification stage and/or controller to set the amplification of the applied RF energy (e.g., how much drive to apply).

In general, the apparatuses described herein may include a user display that is configured to improve display features and enhance ease of use. In addition, the apparatus may include mechanical features to improve cord management, particularly when multiple cords are used. The base unit apparatus may also include one or more features that enhance cooling of the apparatus, including internal cooling channels. These apparatuses may also include comfort-enhancing features for the applicators (e.g., beveled/sloping edges, smooth outer surface, "softer" treatment surface, etc.).

The base unit apparatus, including the controller may operate with one or more class E amplifiers per applicator, which may provide improved efficiency and allowing use of a small and lightweight switching power supply. In general, the apparatus may include an all-digital control.

Load-Specific Applicators

In general, the apparatuses described herein may be configured (tuned) to operate at one or more specific load configurations. These load configurations may adjust parameters within the base unit and/or applicator. The base unit and/or applicator(s) may be configured to switch (manually and/or automatically) between different load configurations. For example, the base unit and/or applicator may be configured to apply the high-energy PEMF to a specific body part (e.g., a patient's foot, arm, knee, hand, torso, leg, etc.). Thus, although the apparatuses described herein may trade off load sensitivity with compact and lightweight features, this tradeoff may be ameliorated by switching between load parameters. For example, an applicator may be specifically tuned for use on a human foot. Thus, in this configuration, the load range may be set within a predefined range. The range may be set empirically, and may be set (via hardware/firmware, etc.) or switched from a look-up table. The range may be determined initially be sampling a population of people to determined expected loads on that body part.

In some variations of the apparatuses and methods described herein, the applicator may be configured with a helical antenna coil, rather than a uniform spiral coil. In some variations the helical coil comprises a trace that spirals around itself but changes diameter, getting wider as it circles outward (see, e.g., FIG. 8D). This spiral may be, in some variations, a logarithmic spiral. In some variation the space between the adjacent lines of the spiraling trace is constant while the thickness of the trace increases. In some variations the spacing between the adjacent lines of the trace varies. Thus, in any of the apparatuses described herein the applicator antenna coil may be a helical coil in which the coil starts thinner in middle and gets bigger as you circle out. This configuration may minimize the effect of the loading on the applicator.

In some configurations the load configurations of the applicator is adapted to be used with a particular body part. For example, the applicator may be configured to be applied specifically to a foot, hand, head, neck, arm, wrist, leg, torso, knee, etc.

For example, in some variations the applicator is configured to have a load that is adapted to be approximately 50 ohms, so that, when driven by the base unit, the applicator sees a load of about 50 ohm real and 0 imaginary; specifically, the cable connecting the applicator to the base unit should see about 50 ohms real and 0 imaginary. The voltage standing wave ratio (VSWR) may be less than about 2.0, and the load characteristics of the applicator may be configured so that the applicator is tuned to the expected load. If the applicator is applied to the wrong load (e.g., to a different body part), then then the apparatus may indicate that the applicator is not in contact with the correct body part. For example, the applicator may indicate that no load (if in air) or that an incorrect body part (e.g., "not the foot") than the body part for which the load was tuned in the applicator (e.g., an applicator, etc.).

In general, any of the apparatuses described herein may be configured to monitor the load seen by the applicator. This may be accomplished by measuring field strength. The sensed field strength may be used to set the drive level. If the applicator is applied outside of the select range, the apparatus may give a feedback error. For example, if the apparatus sees the wrong load (e.g., when an applicator tuned for a foot is applied to a lower back, for example), the load is mismatched, and the efficiency of the field will be outside of a predicted range, which may result in the apparatus indicating an error. Thus, the apparatus may, but does not need to specifically measure the load, but may instead use the field strength. If the load is mismatched, the field strength will be outside of the expected range and the apparatus may have to drive harder to try and achieve the target field strength. This may therefore result in an error, as described above, including an indication that the applicator is being applied to the incorrect body region (or is in air). This message may be presented to the user (e.g., on the output of the base unit) and/or may be stored and/or transmitted, and may be used for patient monitoring (e.g., compliance monitoring). For example, if there is a no-load condition on the apparatus, the apparatus may determine if the device is actually being used (or is in air), or is being used correctly. This may indicate compliance information.

In general, the apparatuses described herein are configured to drive more than one applicator, including two (dual applicators) or more. In some variations, the apparatuses described herein are configured to provide high-power PEMF in which the ratio of the H-field to the E-field being applied is different. For example, H-field may be greater than the E-field seen by the tissue from the applicators described herein. The antenna of the applicator may include one or more materials that reduce the E-field preferentially compared to the H-field. In some cases materials that are absorptive to E-field but not H-field may be placed between the applicator radiator coil and the patient treatment surface in order to reduce the H- to E-field ratio.

The inventors have found that relatively lower E-field (higher H-field) may have a statistically significant effect on the tissue. For example the application of energy seen by the tissue that has a greater than 50% H-field (a ratio of H-field to E-field of greater than 1), such as a greater than about 60% H-field, greater than about 65% H-field, greater than about 70% H-field, greater than about 75% H-field, greater than 80% H-field, etc. Even the lower E-field application of energy (e.g. less than 40%, less than 30%, less than 25%, less than 20%, etc.) the relatively higher H-field application of energy shows a statistically significant response. Thus, varying the amount of the H-field to E-field applied (e.g., by controlling the dielectric properties and permittivity of the applicator), may be advantageous, and may also result in significant power savings (e.g., preferentially applying an H-field to E-field ration of between about 1.1× to 10× the H-field compared to E-field, such as between about 1.2× to 8×, between about 1.5× to 5×, etc.). As the E-field to H-field ratio approaches zero, the power transfer is to the tissue may be more efficient by virtue of the H-field.

The apparatuses described herein may apply energy (PEMF energy) at any appropriate carrier frequency. The carrier frequency may be, for example, approximately 27 MHz. In some variations, the carrier frequency is 27 MHz (e.g., 27.12 MHz) may be used with a stimulation pulse width of 42 microseconds (us) at a 1 kHz pulse rate; stimulation may be applied continuously for 30 min, e.g., twice a day. In this example, the higher energy applied includes and H-field of about 10 A/meter and an E-field of about 200-250 V/m.

When multiple applicators are being used, the two applicators may be synchronized for concurrent operation in a manner that does prevents interference between the two. For example, the base unit may multiplex the applied signals, as mentioned above. Thus, in operation, the apparatus may alternative high-energy PEMF between the left, then right applicators.

In general, the apparatuses described herein may include a controller that is configured for active, closed-loop operation based on the field strength. For example, the controller (processor) of the base unit may be configured for closed loop control of operation to apply high-power PEMF to one or more applicators. As mentioned above, the controller in the base unit may receive feedback based on the driven load (and/or field strength) applied. This data may be used to control operation of the apparatus. When multiple applicators are used, the controller may monitor the load and/or field strength on each applicator and may adjust the output so that multiplexing is suspended when one of the applicators is outside of the predetermined range. Alternatively, the applicator may continue multiplexing, but may suspend the application of power to the applicator that is outside of the target range (e.g., does not have an appropriate load and/or field strength). In some variations, the feedback value is a measure of the field strength; the load seen by the applicator may be derived from the field strength. Conversely the feedback may be the load, and the field strength may be derived. Thus, in some variations, field strength may be directly measured. Field strength measured may be one or both of E-field or H-field. Alternatively or additionally, the apparatus may detect capacitive coupling of the applicator (e.g., to a body part). In some variations, the apparatus may detect the field strength and may use this detected field strength to calculate the applied energy.

Communications Circuitry

Any of the high-power pulsed electromagnetic field (PEMF) applicator systems described herein may be configured for wireless connectivity. In particular, the apparatuses described herein may be configured to include or operate with a cellular link that provides the capability to transmit compliance data (e.g., date, time, and applicator loading) for each user treatment, and/or device diagnostic data (e.g., status of power levels, display module, RFID module, memory, base unit temperature, etc.) to a remote processor, including a cloud data system, either directly or indirectly through a local computing device, such as a smartphone, tablet computer, laptop computer, or desktop computer. In other embodiments, as further described below, the cellular module can be replaced with or modified to include a more general wireless communications module that can utilize a wireless communication protocol, such as Bluetooth or WiFi, to communicate with another device, such as a desktop computer, smartphone, tablet computer, and/or laptop computer. In addition to compliance monitoring, this system may allow for remote troubleshooting and error correction. The wireless (e.g., cellular or Bluetooth) link may also allow for electronic message delivery to the client and downloading of software updates when needed. In some variations patient-specific prescriptions can be delivered wirelessly (e.g., through the cellular link or Bluetooth) to the apparatus.

The apparatuses described herein, despite being configured to delivery very high-energy PEMF signals to multiple applicators, may be small and lightweight. In general, these apparatuses may include an embedded processor that can execute instructions and/or operate via wireless connection (e.g., cellular connection or Bluetooth) to increase data storage and processing power, and may increase the efficiency, features and capabilities.

In some variations, the apparatus is configured to transmit information about the most recent prior use(s) upon activation (turning on) of the apparatus. For example, when the apparatus is turned on, use data (including, but not limited to compliance feedback) may be transmitted. This may allow the apparatus to adjust the next treatment (e.g., how the user is using it) based on the prior treatment data. This configuration may also provide diagnostic data, which may be used to indicate that the unit is functioning properly. For example, if the prior use data indicates that the unit is compromised, it may indicate that it should be replaced, and may be replaced immediately and/or may transmit information to the party responsible for maintaining the unit to replace or service it. In some variations the unit may present a message or messages to the user, either via the screen on the unit, or by calling or messaging (e.g., text messaging) the user with feedback, such as instructions to call the servicing party (including contact information for the servicing party).

In any of these apparatuses, the device may be configured to transmit the prior session at the start of the next treatment and may suspend or prevent the start of treatment until the data has either been transmitted or until at least some minimum number of attempts (e.g., 2 attempts, 3 attempts, 4 attempts, etc.) have been made, before the apparatus is released to allow treatment. Failed attempts may be collected and transmitted together later, including at the next power-up or prior to powering down.

In some variations the apparatus may be operated using a prescription service. When a prescription service is used, the unit may configured to permit delivery of a certain (predetermined) number of treatments per prescription, or a number of daily treatments for a predetermined number of days. The apparatus (e.g., controller) may be configured to display and/or otherwise indicate to the under the number of treatment days/times left, and may also be configured to indicate that the user should contact their physician or health care provider to modify or extend a prescription.

The apparatuses described herein may also be configured to automatically receive, via the wireless circuitry, software upgrades.

In general, the apparatuses described herein may be configured for compliance monitoring. For example, the apparatus may report back information about the use, including the duration of operation, the field strength applied, the time of day, number of times/day used, etc. This data may be stored on the apparatus and/or transmitted to a remote processor/server for further analysis and/or for reporting to the patient's physician (or to a patient's medical record). Compliance monitoring may provide feedback values (digital and/or analog) that may be transmitted back via a data link, such as the wireless (e.g., cellular or Bluetooth) data link. This compliance data may indicate when the user turned the apparatus on, what the load on the apparatus was and/or if this load was appropriate for the expected tissue (and/or if it corresponded to air, or some other tissue). Thus, the compliance data may indicate that the apparatus was turned on, and/or if the apparatus was used.

In some variations some or all of the use (or compliance) information may be transmitted to the apparatus manufacturer or distributer or any other party responsible for maintenance of the apparatus. For example, the apparatus may indicate that the device is not being operated within desired parameters, or the device is not operating properly, or that the user is not operating the device properly. In some variations the base unit may process this information, which may be analyzed locally (in the base unit) and/or remotely (e.g., in a remote processor) to determine if a technician should review the apparatus. For example, one or more use conditions may trigger contact with the party responsible for maintenance of the apparatus, who may receive a notification directly from the apparatus (e.g., via the wireless connection in the apparatus) or indirectly (via a remote processor). For example, if the apparatus determined from the use data that the load is not within the expected range during operation of the apparatus, the apparatus may use the cellular module to contact the party responsible for maintaining the apparatus; a technician may then contact the user to investigate what is going on. Similarly, the device may report an error if one the onboard peripheral devices fails to communicate serially with the processor such as the LCD Display, Cellular Modem, RFID Module, or Real Time Clock. Additionally, a micro SD card that fails or contains invalid calibration data or an RF Board voltage regulator failure may report an error.

Examples

Figure 2:
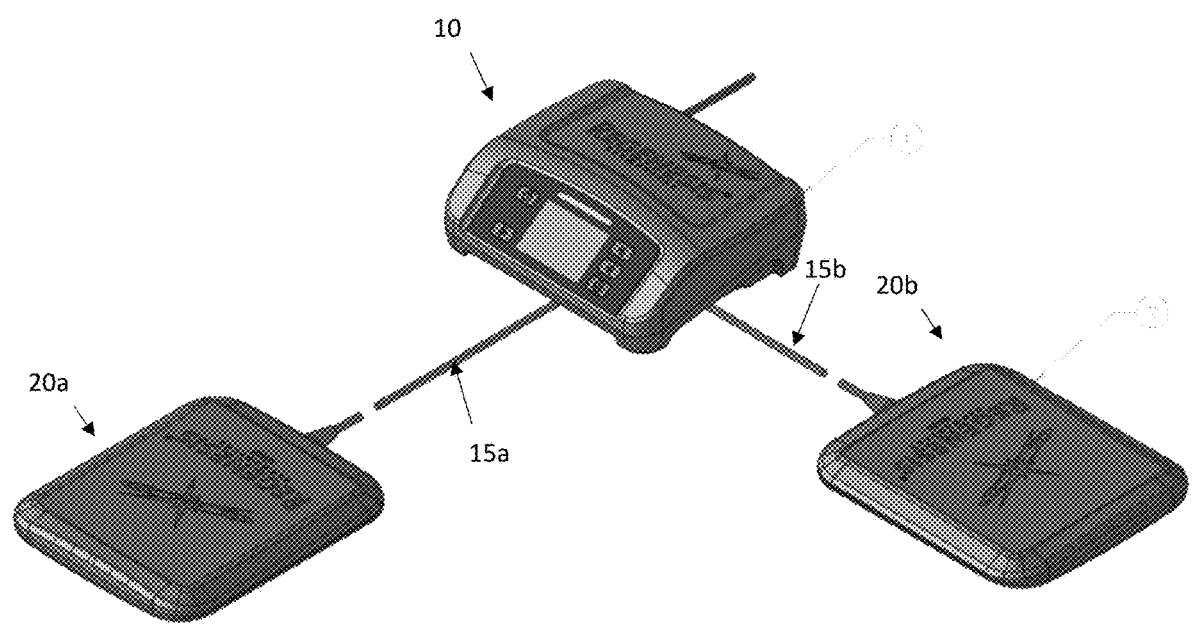
FIG. 2 shows an example of a block diagram of a high-power pulsed electromagnetic field (PEMF) applicator system including a pair of connected applicators.

FIG. 1 illustrates one example of a high-power pulsed electromagnetic field (PEMF) applicator system 100 in one embodiment. As shown in FIG. 1, the systems 100 can include a base housing 10 housing a controller (not shown in FIG. 1) that is configured to generate a low-power control signal and one or more applicators, (e.g., 20a, 20b) coupled to the base housing 10. For example, the base housing 10 is coupled to the one or more applicators (e.g., 20, 20b) by one or more cables (e.g., 15a, 15b). For example, one applicators 20a is shown in FIG. 1. FIG. 2 shows an example with two applicators 20a, 20b where the base housing 10 is coupled to the two applicators 20a and 20b a by two cables 15a and 15b.

Each applicator (e.g., 20, 20b) can apply a high-power, pulsed electromagnetic field signal based on the applied control signal, which may be multiplexed to avoid interference as described above. The high-power pulsed electromagnetic field signal can have a power of greater than 40 W on each applicator. The applicator (e.g., 20a, 20b) can further include a coil antenna circuit configured to emit or apply the high-power pulsed electromagnetic field signal. For example, the one or more applicators can be configured to be hand-held or wearable for the convenience of treatment. The one or more applicators can be applied to the back, the feet, the hand, the shoulder, or any other parts of the body of the patient.

Figure 3A:
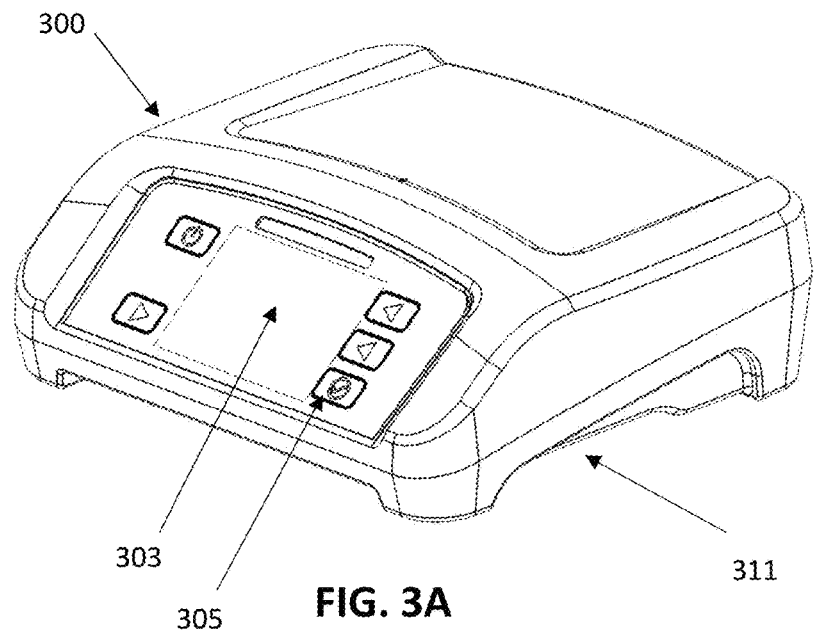
FIGS. 3A-3D schematically illustrates a base unit portion of a high-power pulsed electromagnetic field (PEMF) applicator system.
Figure 3B:
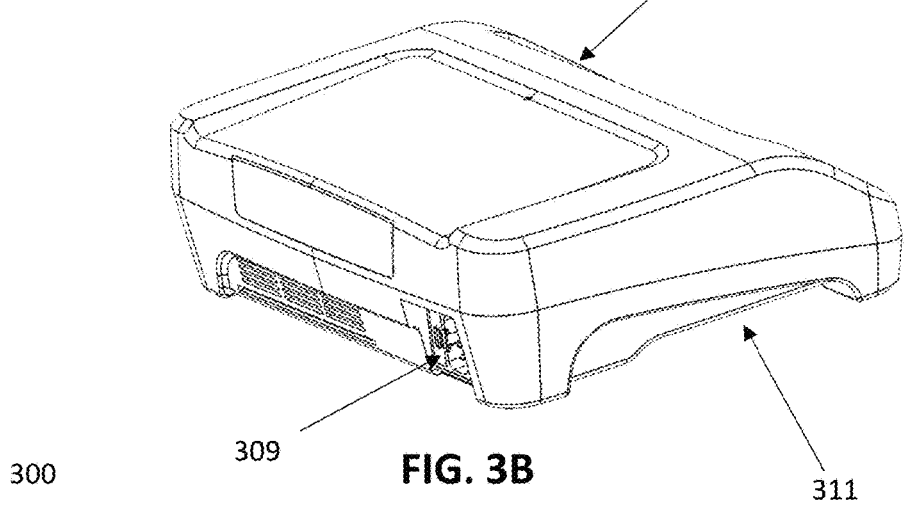
Figure 3C:
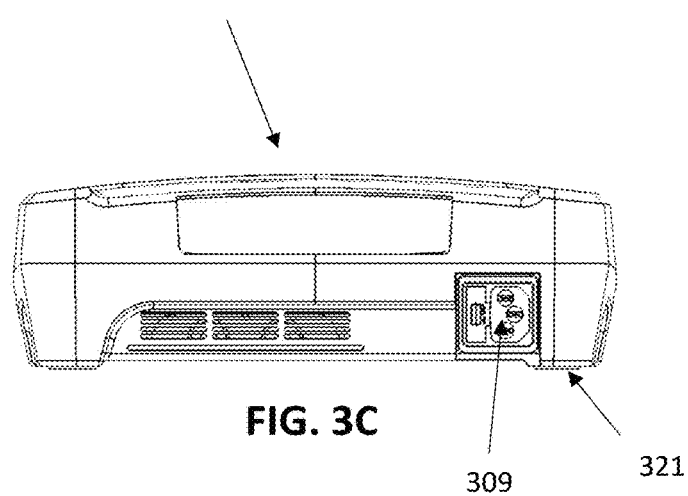

FIGS. 3A-3D illustrate an example of a base unit 300 that is configured to apply or provide high-power PEMF waveforms to one or more applicators. In FIG. 3A, the front perspective view of the base unit 300 shows a screen/display 303 and a plurality of control buttons 305. The screen may be a touch screen. The housing of the base unit may be compact, and may be configured to enhance airflow and therefore cooling of the internal components. Further, the apparatus may be ergonomically configured (having no sharp edges) and be configured to prevent water damage to the high-voltage internal components. FIG. 3B shows a back view showing connections to a power source (e.g., wall power), although other or additional power sources (rechargeable battery, etc.) may be used. FIG. 3C shows a back view. The base unit may be configured to stand above the surface on which it resides by a minimum clearance of about 0.5 cm (e.g., 0.6 cm, 0.7 cm, 0.8 cm, 0.9 cm, 1.0 cm, 1.1 cm, 1.2 cm, etc.). This clearance 311 may allow air circulation for the bottom-facing fan, as well as speaker outlet. The housing may also include one or more vent inlets at or near the front top of the housing. Three or more feet 321 (four are shown in this example) may hold the bottom above the resting surface.

Figure 3D:
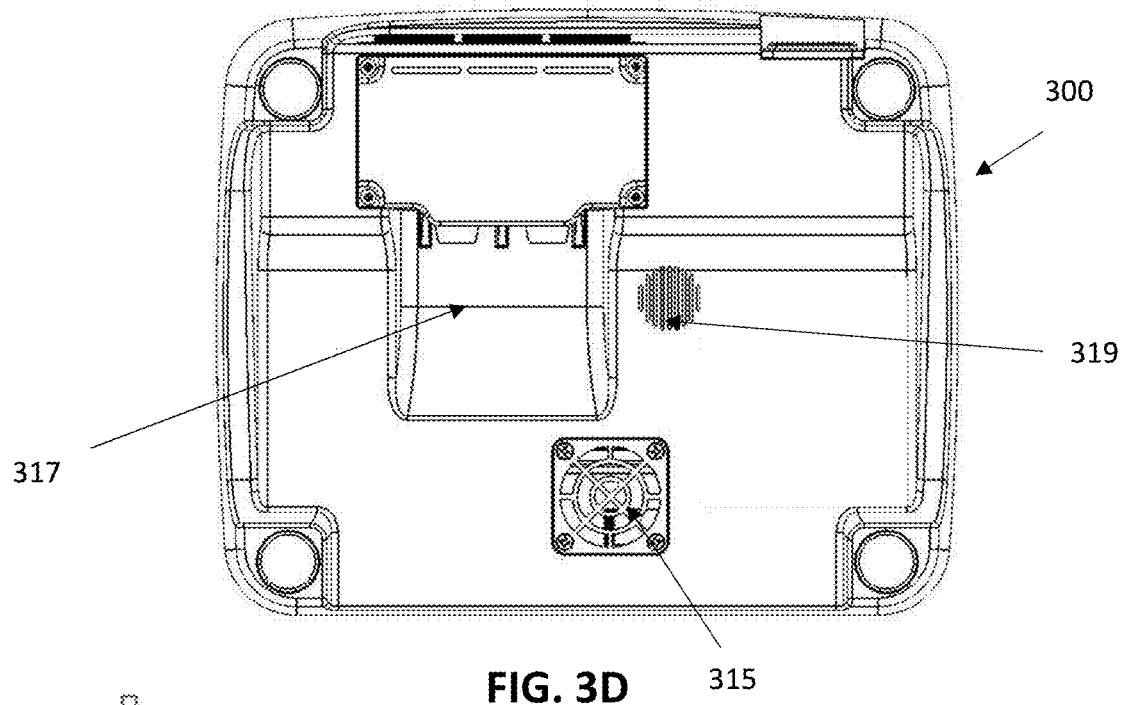

FIG. 3D shows a bottom view of the high-power pulsed electromagnetic field (PEMF) applicator apparatus, showing the cooling fan outlet 315, speaker outlet 319 and a cable management region 317 for coupling to and securing the cables connecting to the applicators (not shown).

Figure 4A:
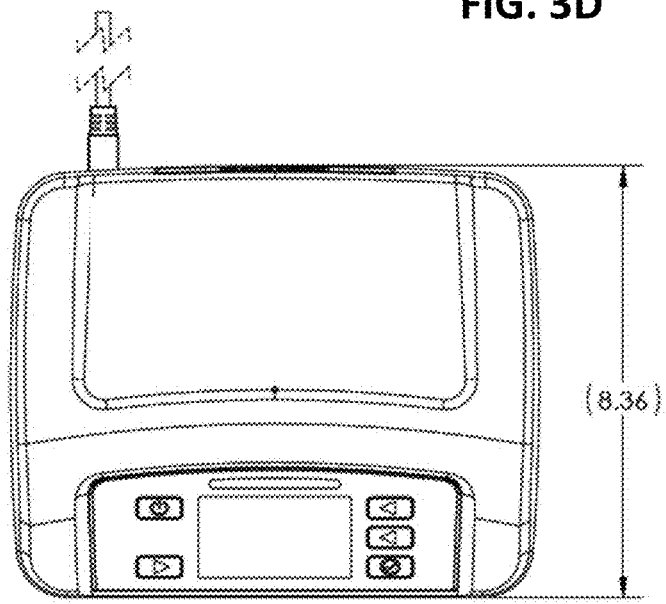
FIGS. 4A and 4B illustrate exemplary dimensions (in inches) for the base unit of FIG. 3A-3D.
Figure 4B:
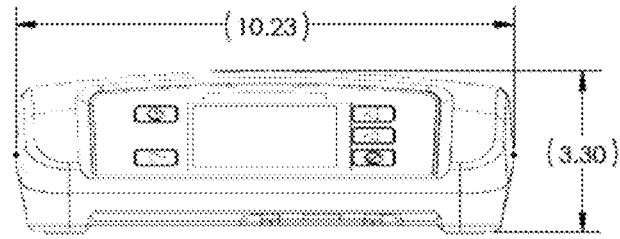

FIGS. 4A-4B illustrate exemplary dimensions for an apparatus similar to that shown in FIGS. 3A-3D. These dimensions (shown in inches) are exemplary only, and may be +/−50%, 40%, 30%, 25%, 20%, 15%, 10%, 5%, etc.

Figure 5:
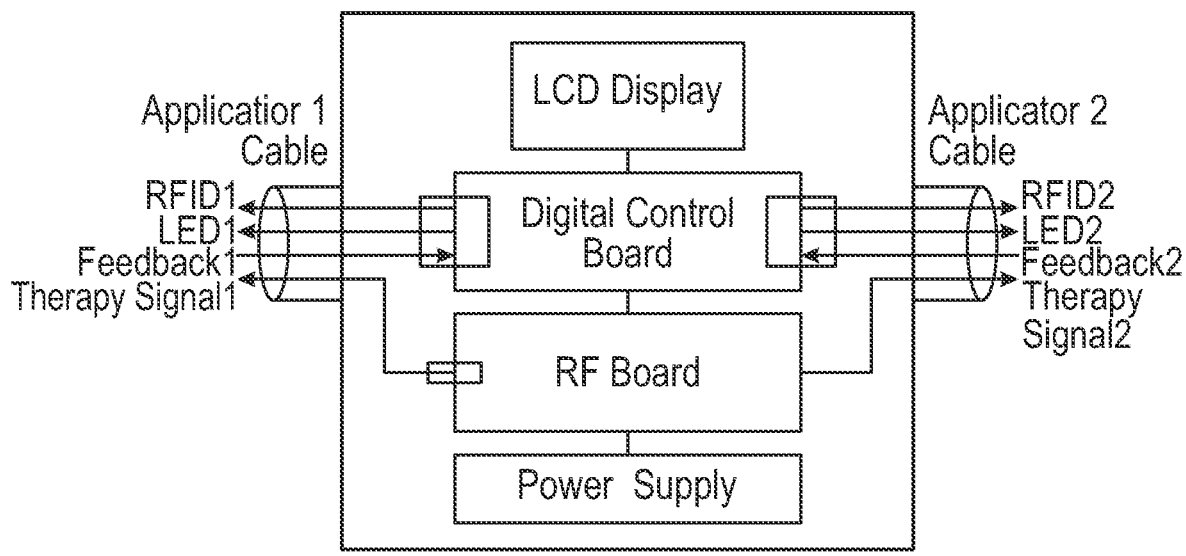
FIG. 5 schematically illustrates one example of a control circuit for a base unit for a high-power pulsed electromagnetic field (PEMF) applicator system.

FIG. 5 schematically illustrates an example of a block diagram of the base unit of a high-power pulsed electromagnetic field (PEMF) applicator apparatus. The block diagram includes a display (LCD display), a controller (including a digital control board), and an RF board, all of which may be connected to a power supply, which may include circuitry (power control circuitry) for providing the power both to operate the circuitry as well as to apply to the applicators. A pair of applicator cables (applicator cable 1 and applicator cable 2) are shown, which may connect to each of two applicators and may carry both power ("therapy signal 1" and "therapy signal 2") and data (e.g., RFID information 1, LED power, feedback from the applicator). The feedback may be, for example, field strength, etc.

Figure 6:
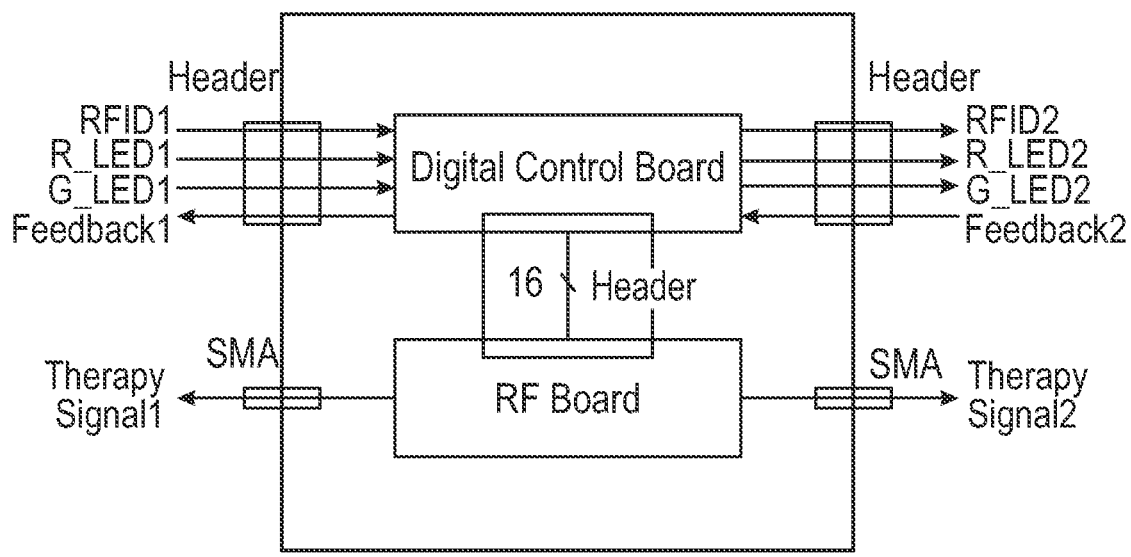
FIG. 6 schematically illustrates another example of a base unit for a high-power pulsed electromagnetic field (PEMF) applicator system, similar to that shown in FIG. 5.
Figure 7:
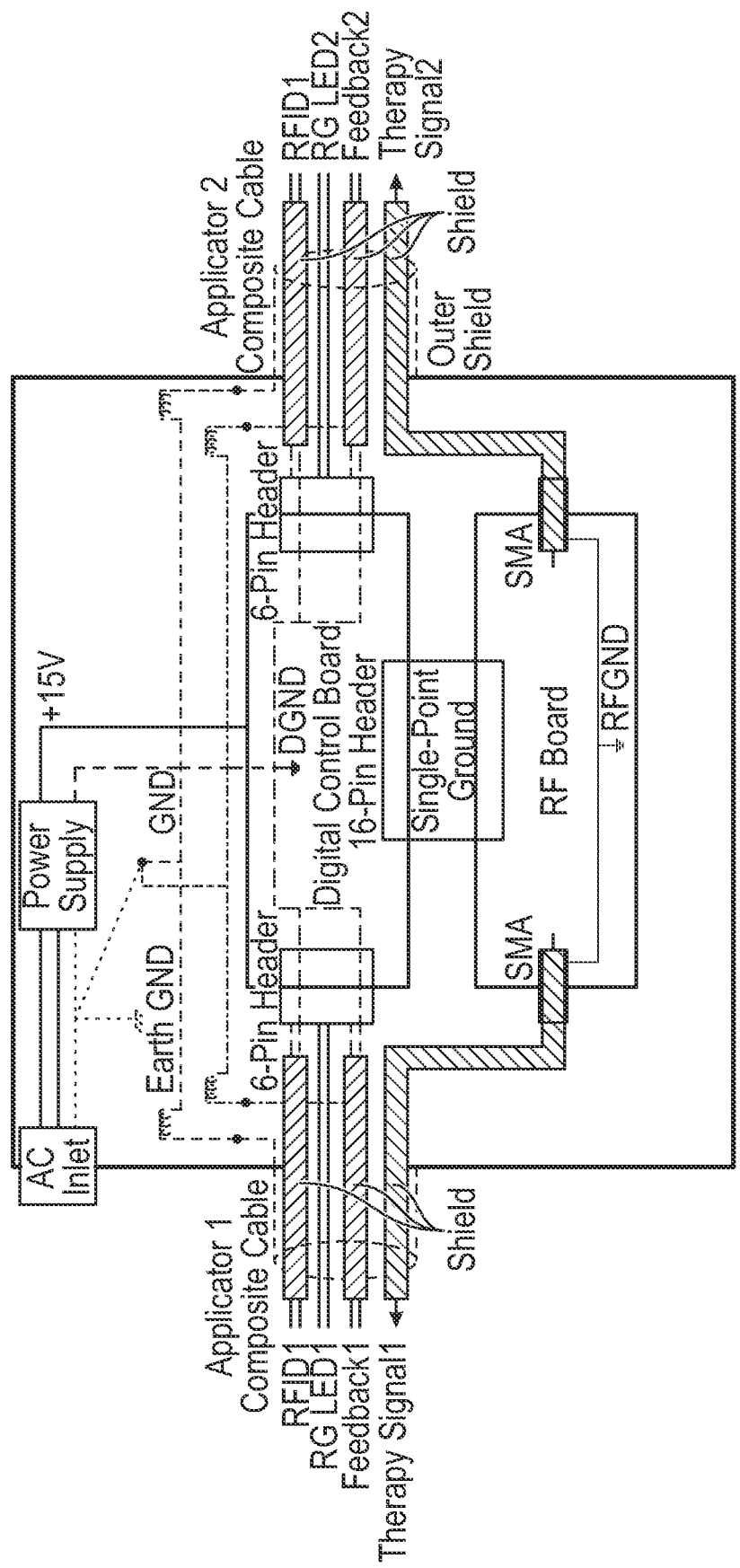
FIG. 7 schematically illustrates one example of a grounding diagram design for a high-power pulsed electromagnetic field (PEMF) applicator system.

FIG. 6 is another schematic of an applicator interface shown the signal processing between the digital control board, the applicators, and the RF board. Generally, data is transmitted to/from the digital control board (controller/processor) and power is applied as a signal (PEMF signal) to the applicator by the RF board. FIG. 7 shows a ground diagram for one example of a high-power pulsed electromagnetic field (PEMF) applicator apparatus. In this example the power supply, control circuitry (digital control board), RF board and applicators are all grounded by the common ground form the AC inlet. All of the cables are shielded cables with the shields being grounded. Finally shielding in the applicator is also grounded to the same common ground.

Figure 8A:
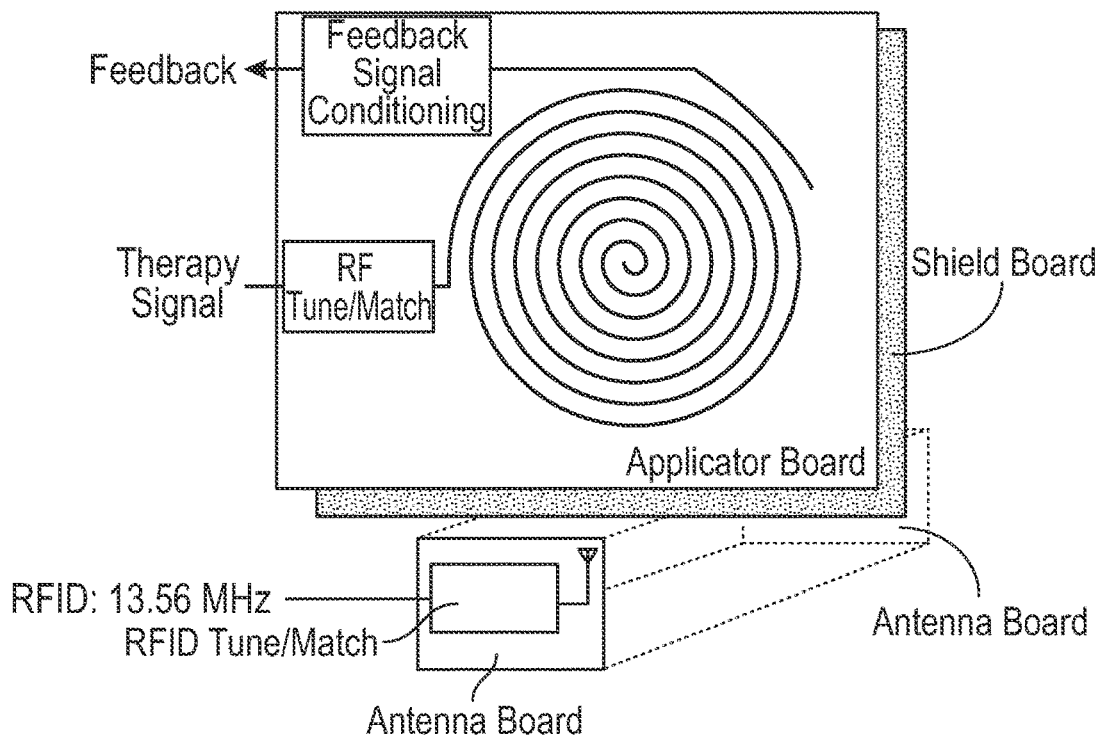
FIG. 8A schematically illustrates one example of an applicator for a high-power pulsed electromagnetic field (PEMF) applicator system.
Figure 8B:
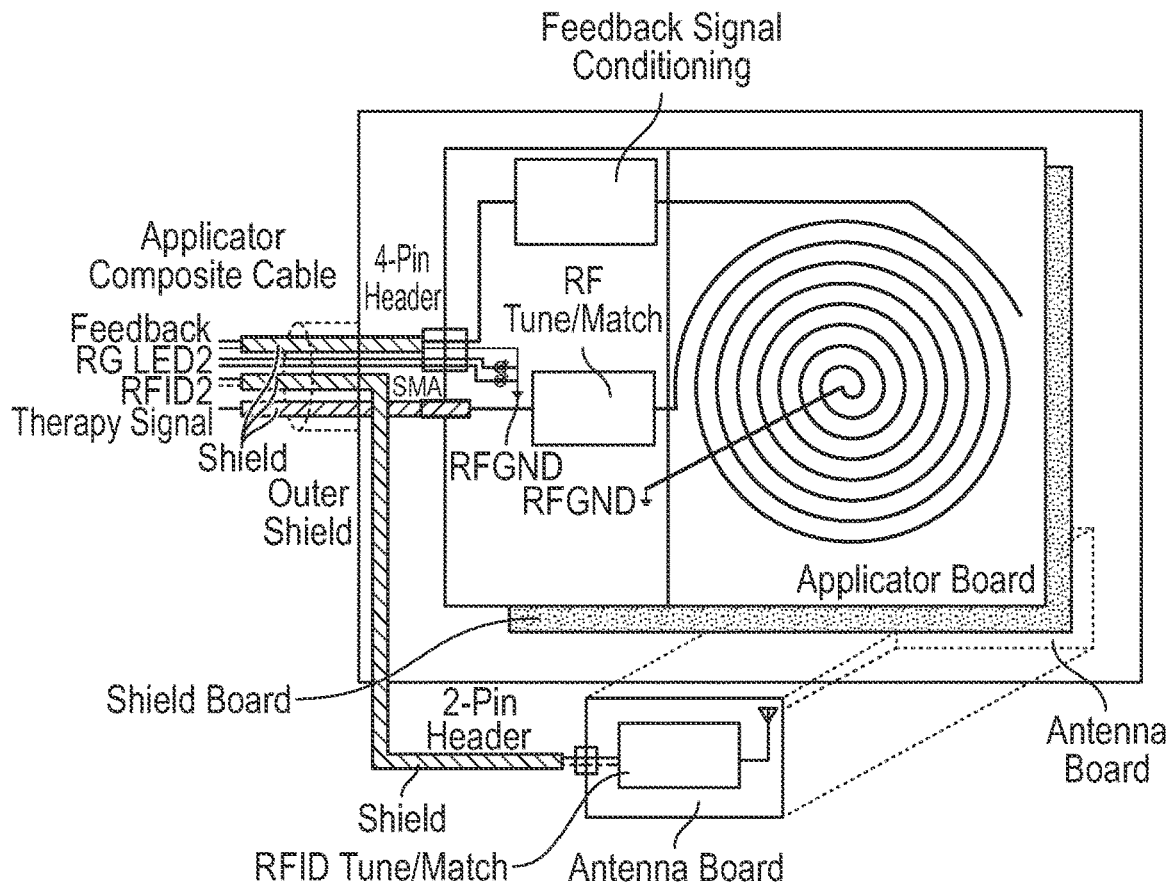
FIG. 8B is another schematic of the applicator of FIG. 8A, showing a grounding diagram with cabling connections, similar to FIG. 7.
Figure 8C:
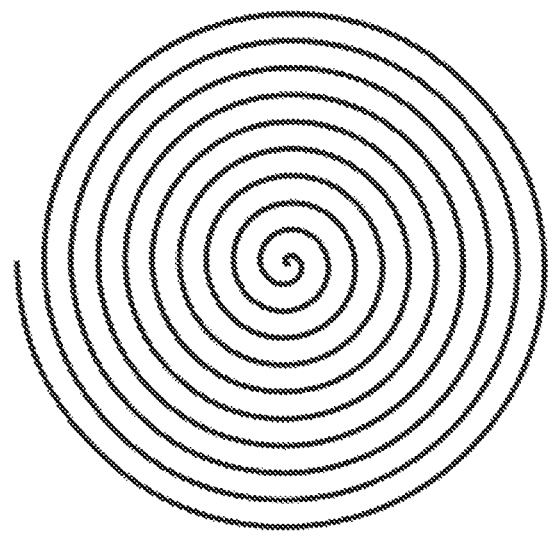
FIGS. 8C and 8D illustrate examples of applicator antenna coils that may be used.
Figure 8D:
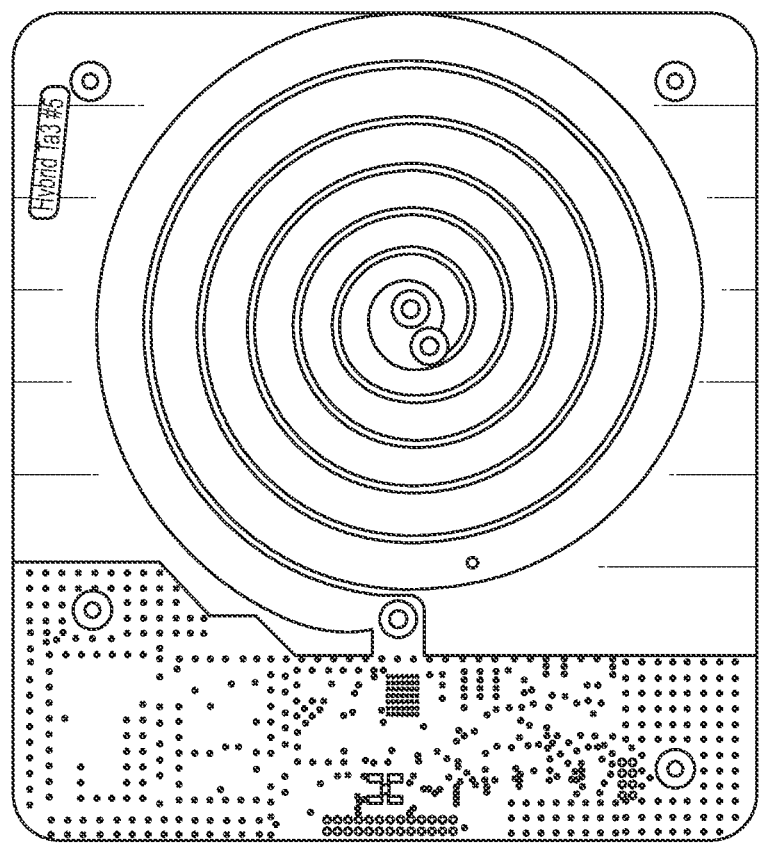

FIGS. 8A-8B schematically illustrate applicators for one example of a high-power pulsed electromagnetic field (PEMF) applicator apparatus. In this example, the apparatus includes an antenna for delivery of the high-energy PEMF energy. The antenna may be a coil, such as shown in either FIG. 8C or 8D. The applicator may also include a feedback signal sensor ("feedback signal conditioning") that may be used in a closed-loop manner to adjust the applied energy, including detecting field strength and/or load. The schematics in FIGS. 8A and 8B also shown the applicator board on which the antenna is positioned. A shielding board is positioned behind the applicator board and a separate antenna board, which may include an RFID tuner may be located on the separate applicator board.

Figure 9:
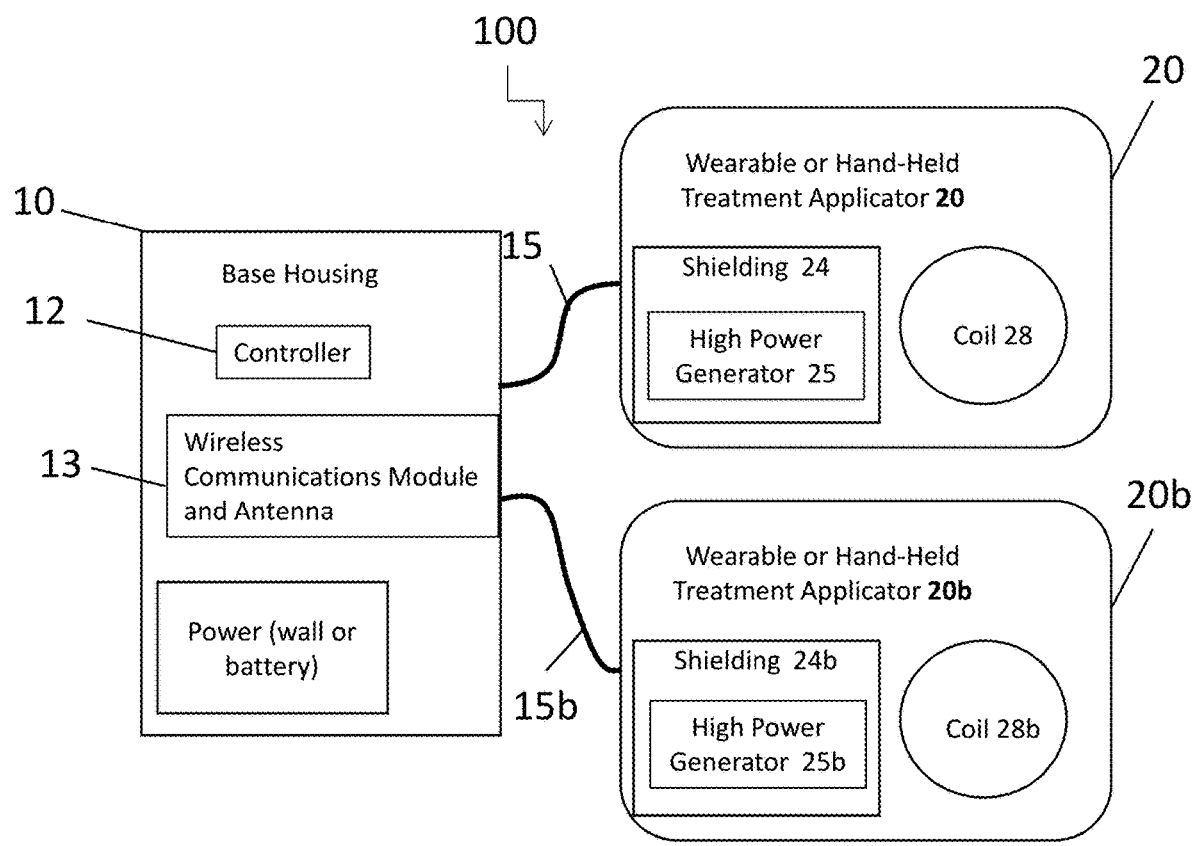
FIG. 9 illustrates a schematic of an embodiment of the PEMF system with wireless communications capabilities.
Figure 10:
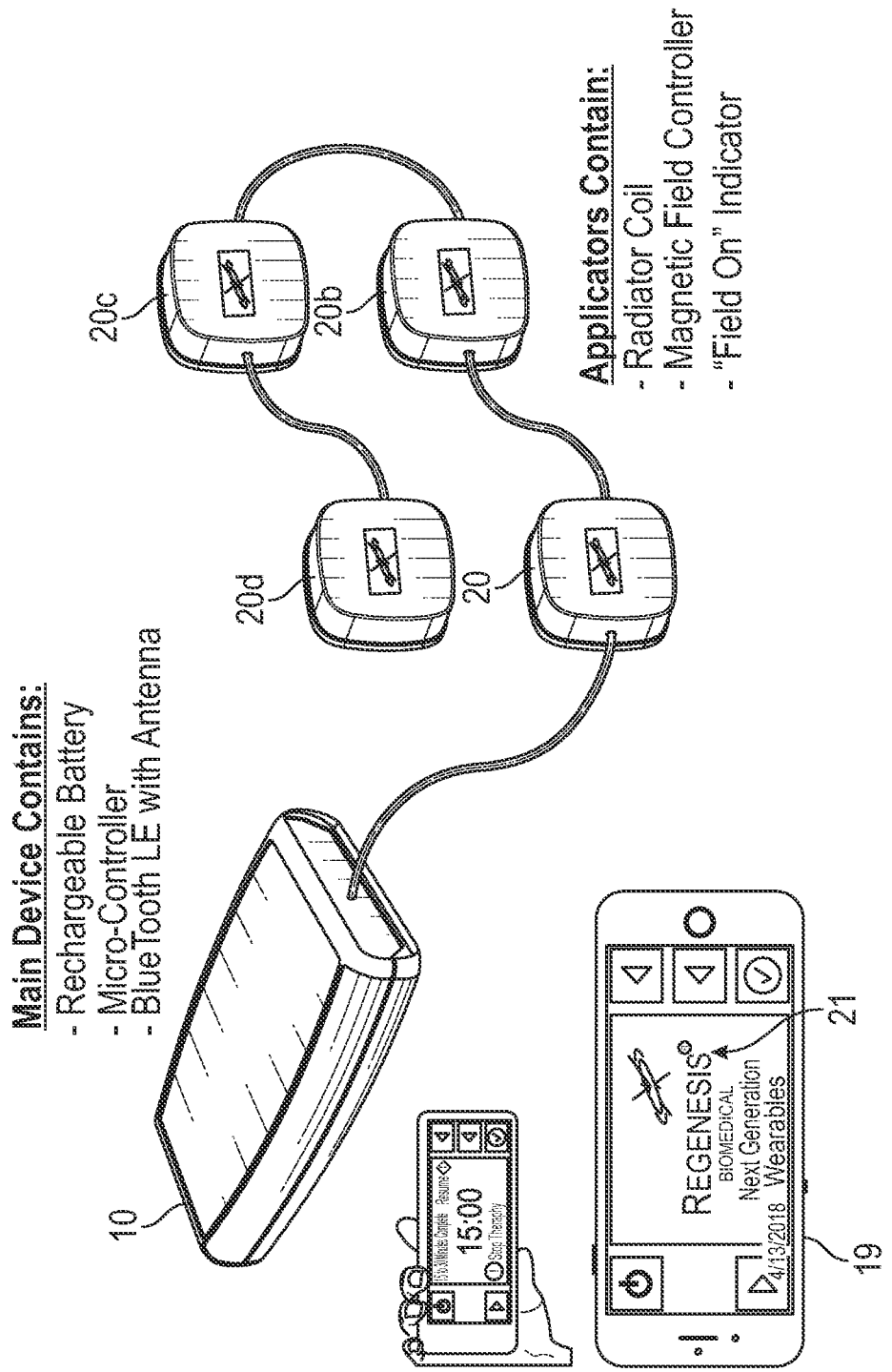
FIG. 10 illustrates an embodiment of a PEMF system with wireless communications and a smartphone for controlling the system.

FIGS. 9 and 10 illustrate an embodiment of a pulsed electromagnetic field (PEMF) applicator system 100' that incorporates a wireless communications module 13 into the base housing 10. The wireless communications module 13 can use any suitable wireless communications protocol, such as Bluetooth or WiFi, for example. The wireless communications module 13 allows the base housing 10 to communicate with one or more computing devices 19, such as a smartphone, tablet computer, laptop computer, and/or desktop computer. This allows the display 21 and user interface to optionally be moved from the base housing 10 to the computing device 19. In some embodiments, the base housing 10 may also include a full display or a rudimentary display and/or user interface. Moving the display 21 from the base housing 10 to the computing device 19 reduces the cost, power consumption, size, and weight of the base housing.

In some embodiments, the base housing 10 and/or the applicators 20, 20b, 20c, 20d can be wearable, especially after reducing the size and weight of the base housing by removing the display and reducing the size of the rechargeable battery. The base housing can include a strap, clip or other fastening mechanism to reversibly attach the base housing to the user. The applicators can be fastened to the body part using an adhesive, strap, or other fastening mechanism. In some embodiments, the applicators can include a on/off indicator 23 that can indicate when a field is being generated by the applicator. The indicator 23 can be a LED that light up when "on" and is dark when "off."

The display and user interface on the computing device 19 can be easily updated and/or modified by updating the mobile application or software on the computing device. This allows improvements in the user interface, which can be an intuitive graphical user interface, to be easily transmitted to the end user so that the end user can utilize and benefit from the latest improvements. Implementation of a graphical user interface typically requires more advanced and costly displays, so by moving the display to the computing device 19, substantial cost savings can be realized in the base housing 10. The computing device 19 can be used to control operation of the base housing 10 and applicators 20, 20b, 20c, 20d using, for example, an intuitive graphical user interface. The display can also be use for displaying data related to the prescribed treatment regiment, device performance data, past device usage data, upcoming schedule treatment sessions, compliance data, and all the other types of data described herein. The data can be presented in text form, in tables, in graphs, and/or in charts.

The wireless communication between the base housing 10 and computing device 19 also allows data to be transmitted between the base housing 10 and computing device 19. For example, software and/or firmware updates can be transmitted from the computing device 19 to the base housing 10 so that the base housing 10 can be remotely updated with the latest software and/or firmware. In addition, the base housing 10 can transmit device operation data to the computing device 19, which can then transmit the device operation data through a cellular network, an internet connection, and the like, to a remote computing device, such as a server, or a cloud computing network that is maintained by the device manufacturer. The device operation data can include treatment data such as when the device was used for treatment, how long the device was used during treatment, and other treatment parameters such as stimulation intensity/power and the carrier frequency used.

The data received by and stored in the remote computing device or cloud computing network can be used to monitor and evaluate patient compliance with a physician prescribed treatment plan as describe above. For example, the data can include whether the patient has missed any scheduled treatments, whether any treatment sessions were only partially completed, and whether the appropriate treatment parameters were used.

To prevent overuse of the system, the controller in the base housing may be configured to limit the amount of treatment that can be applied to the patient over a specified time period, such as a day, week, or month. The computing device and/or the remote computing device can additionally or alternatively have the ability to restrict device overuse based on the received device use data.

In some embodiments, the patient's health care provider(s) can access, review, analyze, and/or comment on the data on the remote computing device or cloud computing network, and can modify one or more treatment parameters based on the review and/or analysis of the data, and the updated treatment parameters can be transmitted from the remote computing device or cloud computing network to the local computing device (e.g. a smartphone), and then to the controller of the base housing. The health care provider(s) can access the remote computing device or cloud computing network through an internet connection through a cellular network, a WiFi network, or through a wired connection.

The device usage and performance data, the treatment data, and other data relevant to device performance and treatment compliance can be stored locally in the base housing and/or the local computing device, and also remotely in the remote computing device or cloud computing network. Transmission of the data can be done at prescribed intervals, i.e., every 5, 15, 30, 60, 120, 240, or 720 minutes, or every 1, 2, 3, 4, 5, 6, or 7 days. Alternatively, data transmission can be scheduled at particular times, such as a night when the device is not being used for treatment. In some embodiments, the field generated by the applicators may interfere with wireless data transmission, so data transmission may be restricted or limited to periods when the applicators are not generating any fields.

In some embodiments, the application/software on the local computing device can be operated continuously even when the device is not being used for therapy. When the device in not being used actively for therapy, the application/software may be put in background state or mode to consume less power (i.e., the display can be powered off). In other embodiments, the application/software may only be active when the device is in use for therapy. The user interface of the application/software can include an on/off button, a pause button, a countdown timer that shows the remaining treatment time, and other features described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of controlling operation of a high-power pulsed electromagnetic field (PEMF) applicator system, the method comprising:
   emitting a high-power PEMF signal from an applicator of the high-power PEMF applicator system, wherein the high-power PEMF applicator system includes:
   a controller configured to generate a high-power pulsed signal;
   a power amplifier configured to generate a pulsed drive signal;
   a wireless communication circuit; and
   an RF amplification stage coupled to the applicator, wherein the applicator includes a coil circuit configured to emit the high-power PEMF signal and a feedback sensor;
   receiving a feedback signal in the feedback sensor associated with the high-power PEMF signal emitted by the applicator, wherein the feedback signal is based on a detected field strength of the emitted high-power PEMF signal;
   transmitting a therapy field feedback signal derived from or including the feedback signal to a local computing device;
   determining that the therapy field feedback signal exceeds a predetermined set of performance parameters; and
   transmitting, from the local computing device, an alert to a user operating the high-power PEMF applicator system in response to determining that the therapy field feedback signal exceeds the predetermined set of performance parameters.

2. The method of claim 1, wherein emitting the high-power PEMF signal comprises emitting a high-power PEMF signal having a power of greater than 40 W.

3. The method of claim 1, wherein emitting comprises emitting the high-power PEMF signal from the applicator, said applicator being part of a plurality of applicators coupled to the high-power PEMF applicator system.

4. The method of claim 1, further comprising adjusting the high-power PEMF signal emitted based on the feedback signal.

5. The method of claim 1, further comprising a remote server and transmitting, from the remote server, a prescription for additional high-power PEMF signal to the local computing device.

6. The method of claim 1, wherein receiving the feedback signal comprises receiving one or more of: a capacitance signal and an inductance signal.

7. The method of claim 1, wherein receiving the feedback signal comprises a field strength signal indicating a strength of one or more of an applied electrical field or magnetic field.

8. The method of claim 1, wherein receiving the feedback signal comprises receiving a signal indicating contact with a body part.

9. The method of claim 1, wherein transmitting the alert comprises transmitting via a cellular transmission from the high-power PEMF applicator system.

10. The method of claim 1, wherein transmitting the therapy field feedback signal further comprises transmitting the therapy field feedback signal from the local computing device to a remote server.

11. The method of claim 1, wherein transmitting the therapy field feedback signal comprises transmitting compliance data based on the feedback signal in the feedback sensor.

12. The method of claim 1, wherein transmitting the therapy field feedback signal comprises transmitting in real time.

13. The method of claim 1, wherein transmitting the therapy field feedback signal comprises transmitting at a start of a next session of the high-power PEMF applicator system.

14. The method of claim 1, wherein transmitting the therapy field feedback signal comprises transmitting at an end of a therapy session of the high-power PEMF applicator system.

15. The method of claim 1, further comprising confirming a transmission path before transmitting the therapy field feedback signal.

* * * * *